United States Patent [19]

Takahashi

[11] Patent Number: 4,714,328
[45] Date of Patent: Dec. 22, 1987

[54] OPERATING MICROSCOPE APPARATUS

[75] Inventor: Naoyuki Takahashi, Tokyo, Japan

[73] Assignee: Olympus Optical Co., Ltd., Tokyo, Japan

[21] Appl. No.: 884,668

[22] Filed: Jul. 16, 1986

Related U.S. Application Data

[63] Continuation-in-part of Ser. No. 666,124, Oct. 29, 1984, abandoned, which is a continuation of Ser. No. 326,652, Dec. 2, 1981, abandoned.

[30] Foreign Application Priority Data

Dec. 4, 1980 [JP] Japan .................................. 55-171332

[51] Int. Cl.⁴ ............................................ G02B 21/24
[52] U.S. Cl. .................................... 350/521; 350/522
[58] Field of Search ............... 350/521, 522, 582, 585, 350/587

[56] References Cited

U.S. PATENT DOCUMENTS 2,967,458 1/1961 Stone, Jr. .................. 350/522 X
3,868,171 2/1975 Hoppl .

FOREIGN PATENT DOCUMENTS

OS 3147836 7/1982 Fed. Rep. of Germany .
DE 3147836 2/1985 Fed. Rep. of Germany .
57-94710 6/1982 Japan .

*Primary Examiner*—F. L. Evans
*Assistant Examiner*—Matthew W. Koren
*Attorney, Agent, or Firm*—Cushman, Darby & Cushman

[57] ABSTRACT

An operating microscope apparatus wherein, in order that an operator or accessories with which the operator is equipped may not be likely to collide with a case containing a driving mechanism for moving a microscope assembly during the use, the operatability may be improved and the length from the case top surface to the focal plane of the microscope may be shortened, the case is formed so as to be movable integrally with the microscope assembly in the horizontal plane with respect to a supporting arm, a suspending member for suspending the microscope assembly integrally with the case is arranged so that its center axis may intersect at an angle with a normal passing through the rotation center of the case and the microscope assembly is fitted to the suspending member so that, when the case is in the center position of its moving range, the incident optical axis of the microscope assembly may coincide with the above mentioned normal.

7 Claims, 5 Drawing Figures

4,714,328

OPERATING MICROSCOPE APPARATUS

This is a continuation-in-part of application Ser. No. 666,124, filed Oct. 29, 1984, which was abandoned upon the filling hereof and which was a continuation of Ser. No. 326,652, filed Dec. 2, 1981, now abandoned.

BACKGROUND OF THE INVENTION (a) Field of the Invention

This invention relates to operation microscope apparatus and more particularly to a driving and supporting apparatus for a microscope assembly fitted movably to a stand.

(b) Description of the Prior Art

For example, as shown in FIG. 1, a conventional operating microscope comprises a stand 1, a supporting arm 2 mounted on the stand 1 so as to be movable in the vertical direction and rotatable around the vertical axis, a microscope assembly moving device 3 supported at the tip of the supporting arm 2 so as to be rotatable around the vertical axis, a microscope assembly suspending member 4 fitted to the bottom of the moving device 3 so as to be movable in the X and Y directions in the horizontal plane, a microscope assembly (including a lens barrel, objective and eyepiece) 5 fitted to the suspending member 4, a current source part 6 connected to the moving device 3 and containing a position controlling circuit and a trodden controller 7 connected to the current source 6 so that an operator may make an operation while observing on the focal plane SP of the microscope with the microscope assembly 5 and may move the focal plane SP of the microscope in the X and Y directions by actuating the device 3 by operating the controller 7 as required. However, as this moving device 3 is so formed that the microscope assembly 5 may be movable relatively with the case 3a of the moving device 3, the operator 8 or accessories with which the operator and/or microscope assembly is equipped have been likely to collide with the case 3a. Further, this moving device 3 has had defects that, as the microscope assembly 5 is fitted directly to the bottom of the moving device 3 through the suspending member 4, the distance H from the top surface of the case 3a of the moving device 3 to the focal plane SP of the microscope will be longer and the operatability will reduce. There has been also a defect that, as this moving device 3 is so made that, when the movable member is positioned in the center of the moving range, a slip D will be present between the center axis of the part of fitting to the supporting arm 2, that is, the rotation center axis l of the moving device 3 and the observing optical axis l' of the microscope assembly and the operatability will reduce.

SUMMARY OF THE INVENTION

A primary object of the present invention is to eliminate such defects of an operating microscope as are described above.

According to the present invention, this object is attained by securing a microscope assembly suspending member to a case of a moving device so that this case may be made movable relatively with a supporting arm by a driving mechanism.

According to a preferred formation of the present invention, the microscope assembly suspending member is fitted to the case so that its center axis may intersect obliquely with the normal passing through the rotation center of the microscope assembly suspending member with respect to the supporting arm and the microscope assembly is fitted to the suspending member so that, when the movable member of the moving device is in the intermediate position of its moving range, the incident optical axis of the microscope assembly may coincide with the above mentioned normal. Thereby, not only the entire apparatus will be compact but also, when the apparatus is used, the operatability will be remarkably high.

The movable member is controlled in the movement by the rotation of a lead screw and, when it reaches the limit position of the movement, the rotation of the lead screw will be automaticall stopped. Even if the movable member reaches the limit position of the movement, when the rotation of the lead screw does not stop, the movable member will disengage from the lead screw and will be no longer controlled by the lead screw. Therefore, the moving device will be prevented from being broken and will not be broken while it is being transported.

A plurality of covers movable together with the microscope assembly are arranged as overlapped in steps to cover the top opening of the case in the upper portion of the moving device. These covers have respective bent edges so that the bent edge of each cover may be arranged as opposed to the bent edge of the other cover. Thereby, the dust and moisture can be prevented from entering into the moving device.

This and other objects of the present invention will become more apparent in the course of the following detailed description and appended claims.

DESCRIPTION OF THE PREFERRED EMBODIMENTS

Figure 1:
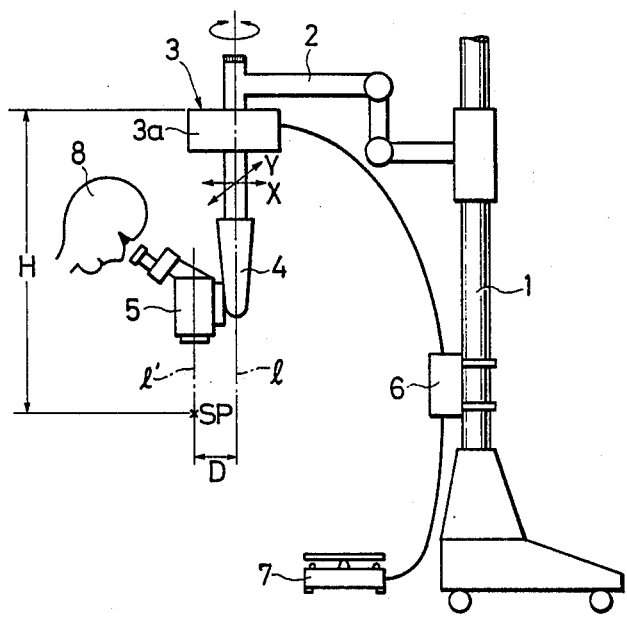
FIG. 1 is a schematic side view of a conventional operating microscope apparatus.
Figure 2:
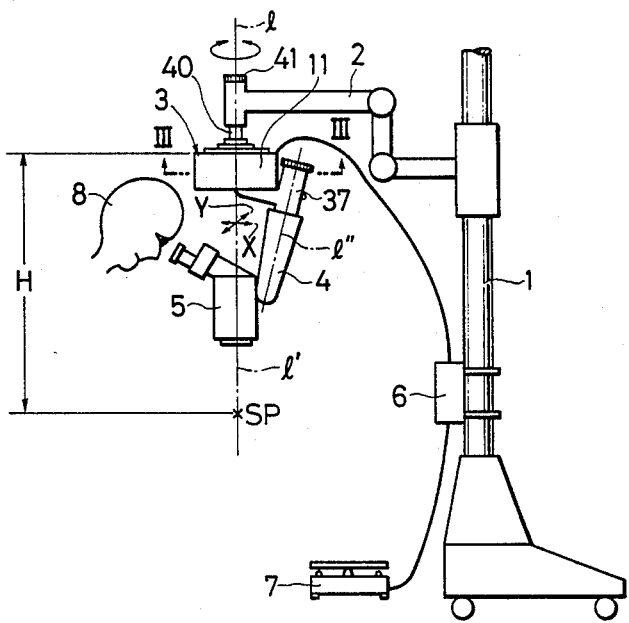
FIG. 2 is a schematic side view showing an embodiment of an operating microscope apparatus according to the present invention.
Figure 3:
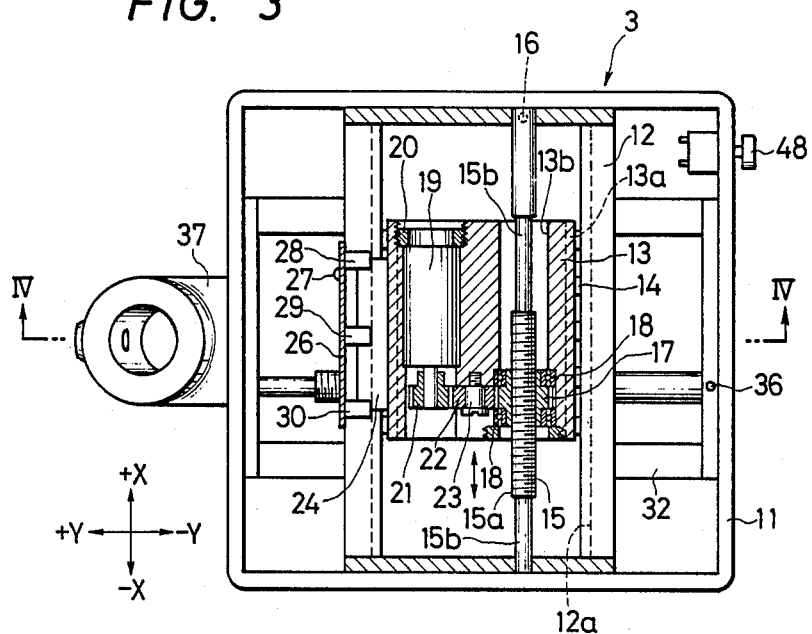
FIG. 3 is an enlarged sectional view on line III—III in FIG. 2.
Figure 4:
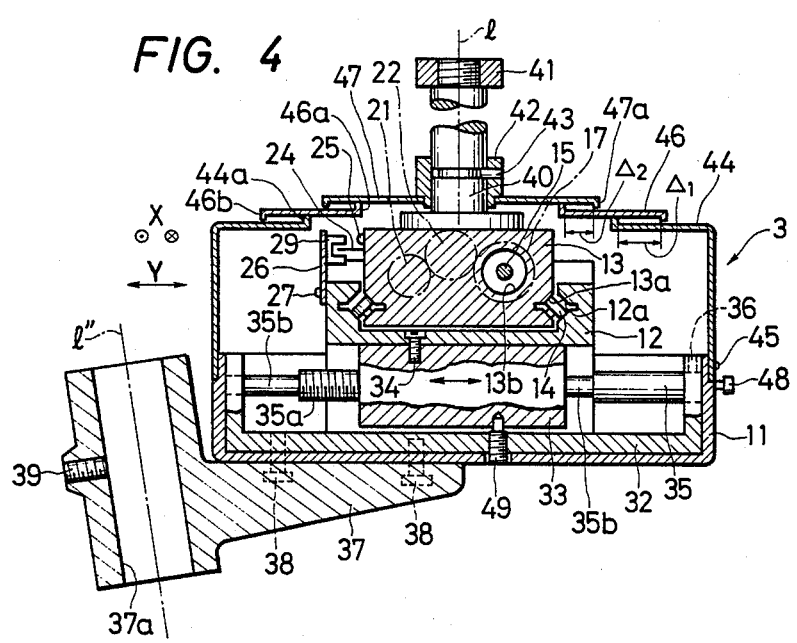
FIG. 4 is a sectional view on line IV—IV in FIG. 3.

The details of the apparatus according to the present invention shall be described with reference to FIGS. 2 through 4 in which the same reference numerals are used respectively for the same parts and portions as are already described with reference to FIG. 1.

The reference numeral 11 denotes a box-shaped case, 12 denotes a rail base slidably arranged between the inner walls of the case 11 and provided with V-grooves 12a parallel with the X-direction respectively on both inside walls, 13 denotes a slider provided with V-grooves 13a parallel with the X-direction respectively on both outside walls facing respectively both inner walls of the rail base and mounted on the rail base 12 movably in the X-direction through a plurality of rollers 14 arranged between both V-grooves 12a and 13a, 15 denotes a lead screw passed through a hole 13b of the slider 13 in the direction parallel with the X-axis, fixed to the rail base 12 by a fixing screw 16 and having screwless shaft portions 15b, 15b of a diameter smaller than that of the screw portion 15a formed in both end portions, 17 denotes a gear supported rotatably concentrically with the lead screw 15 by a pair of radial ball bearings 18, 18 secured on the slider 13 and screwed to the screw portion 15a of the lead screw 15, 19 denotes a motor fixed on the slider 13 by a locking plug 20 and controlled in the rotation by the controller 7, 21 denotes a pinion secured to the rotary shaft of the motor 19, 22 denotes an idle gear pivoted on a pin 23 secured to the slider and meshed with the pinion 21 and gear 17, 24 denotes a blade fixed to the side wall of the slider 13 by a fixing screw 25 (FIG. 4) and inserted at the edge into a groove of later described photocouplers, 26 denotes a supporting plate fixed to the side wall of the rail base 12 by a screw 27 and the reference numerals 28, 29 and 30 respectively denote photocouplers fitted to the supporting plate 26 in the positions corresponding respectively to one limit position (+ limit position), the intermediate position and the other limit position (− limit position) of the movement of the blade 24 and used to detect the position of the blade 24, that is, the position of the slider 13 by reading off the respective output states with the position controlling circuit of the current source part 6. These form an X-direction moving mechanism. The distance between the photocouplers 28 and 29 and the length of the blade 24 are made longer than the entire moving range required by the slider 13. The reference numeral 32 denotes a rail base having a structure fundamentally identical with that of the rail base 12 and arranged along the direction, that is, Y-direction intersecting at right angles with the X-direction between the inner walls of the case 11, 33 denotes a slider having a structure fundamentally identical with that of the slider 13, mounted movably in the Y-direction on the rail base 32 and fixed to the bottom of the rail base 12 by a fixing screw 34 and 35 denotes a lead screw passed through the slider 33 in the direction parallel with the Y-axis, fixed on the rail base 32 by a screw 36 and having screwless shaft portions 35b, 35b of a diameter smaller than that of the screw portion 35a screwed to the slider 33 in both end portions. A moving mechanism and position detecting mechanism of structures fundamentally identical with those of the above mentioned X-direction moving mechanism and position detecting mechanism are fitted to the rail base 32 and slider 35 and they all form a Y-axis direction moving mechanism. The reference numeral 37 denotes a microscope assembly suspending arm fixed to the bottom wall of the case 11 and the bottom wall of the rail base 32 by screws 38, 38 and provided with a fitting hole 37a arranged in the portion projecting outward of the case 11 so that the center axis 1″ may intersect obliquely with the normal passing through the rotation center of the microscope assembly moving device 3 and 39 denotes a screw for fixing the microscope assembly suspending member 4 inserted in the fitting hole 37a to the arm 37. The angle of fitting the suspending member 4 to the microscope assembly 5 is made to coincide with the angle of intersecting the axis 1″ with the normal 1 and the incident optical axis 1″ of the microscope assembly 5 is made to coincide with the normal 1 by properly selecting the length of the suspending member 4. The reference numeral 40 denotes a fitting shaft supported by the tip of the arm 2 so as to be rotatable around the normal 1, prevented from falling down by a nut 41 screwed to its top portion and secured at the lower end to the top surface of the slider 13, 42 denotes a collar fitted to the fitting shaft 40 and prevented by a pin 43 from moving in the axial direction, 44 denotes a first cover fixed to the case 11 by a screw 45, 46 denotes a second cover mounted slidably on an upward bent edge 44a of the first cover 44 and 47 denotes a third cover fixed to the lower end of the collar 42 and mounted slidably on an upward bent edge 46a. When the first cover 44 is displaced with respect to the fitting shaft 40 and its upward bent edge 44a contacts a downward bent edge 46b of the second cover 46, the second cover 46 will be able to move integrally with the first cover 44 until its upward bent edge 46a contacts a downward bent edge 47a of the third cover 47. When the sliders 13 and 33 are in the center positions, if the distance between the upward bent edge 44a of the first cover 44 and the downward bent edge 46b of the second cover 46 and the distance between the upward bent edge 46a of the second cover 46 and the downward bent edge 47a of the third cover 47 are represented respectively by $\Delta_1$ and $\Delta_2$, $2(\Delta_1+\Delta_2)\geqq$ the moving range of the slider 13(33) with respect to the rail base 12(32). The reference numeral 48 denotes a resetting button provided on the case 11 so that the operating part may be exposed out of the case 11 and connected to the position controlling circuit of the current source part 6 and 49 denotes a fixing screw fitted at the tip in a hole made in the bottom of the slider 33, able to be screwed in the stem to the rail base 32 and used as required to prevent the relative movement of the slider 33 and rail base 32.

The operation of the above described apparatus shall be explained in the following. When the controller 7 is operated by foot, for example, to put a +X-direction driving signal into the motor 19, the motor 19 will rotate in the predetermined direction and this rotation will be transmitted to the gear 17 through the pinion 21 and idle gear 22 to rotate the gear 17. With this rotation of the gear 17, the slider 13 will tend to move in the −X-direction but, as the slider 13 is secured to the fitting shaft 40, all the other members (hereinafter, referred as a case block) than the slider 13, fitting shaft 40, nut 41, collar 42, pin 43 and third cover 47 will be moved in the +X-direction. Therefore the microscope assembly 5 will be also moved in the +X-direction as long as the +X-direction driving signal is continued to be put into the motor 19. When the case block thus reaches the limit position, it will be detected by the photocouplers 28, 29 and 30, the detecting signal will be put into the position controlling circuit of the current source part 6 and the feed of the +X-direction driving signal will be interrupted. Therefore, even if the controller 7 is continued to be operated, the rotation of the motor 19 will stop and thereby the microscope assembly 5 will be stopped in the + limit position. In case any or all of the photocouplers become inoperative and the case block reaches the limit position but is not detected, the gear 17 will come and idle on the screwless portion 15b of the lead screw 15 and, as a result, the case block will be no longer able to move and will be therefore prevented from being broken. If the resetting button 48 is pushed, the slider 13 in whatever position with respect to the slider 13 will be automatically returned to such a normal position that the slider 13 is positioned in center of the rail 12 by the position controlling circuit of the current source part 6. Thus, the microscope assembly 5 will be moved in the + X-direction. It is needless to say that, by the same principle, it will be able to be moved in each of the − X, + Y and − Y directions and further in the oblique direction by the combination of the ± X-direction and ± Y-direction.

As explained above, in the present apparatus, as the microscope assembly 5 does not move relatively with the case block, the operator 8 or accessories will be never likely to collide with the case while the apparatus is being used. Further, as the microscope assembly 5 is fitted to the bottom of the case 11 through the suspending member 4 intersecting obliquely with the normal 1 passing through the rotation center of the fitting shaft 40 and the arm 37 holding the suspending member 4, the distance H from the top surface of the moving device to the focal plane SP of the microscope will be short and the apparatus will be easy to operate. Also, in the present apparatus, if the case block is positioned in the center of the moving range by operating the resetting button 48 or the like, the incident optical axis 1' of the microscope assembly 5 will coincide with the rotation center line 1 and therefore the apparatus will be easier to use. Further, in the present apparatus, as the motor is contained in the slider 13, 33 and the gear is rotated instead of the lead screw 15, 35, the dimension in the axial direction of the lead screw 15, 35 may be small in the structure and the entire apparatus will be so compact as to cause no unnecessary pressing feel to the operator. Even if the photocouplers 28, 29 and 30 do not operate, when the case block reaches the limit position, the gear will come and idle on the screwless portion 15b, 35b of the lead screw 15, 35 and, as a result, the case block will be no longer able to move and will be therefore prevented from being broken. As the first cover 44, second cover 46 and third cover 47 are overlapped in steps so that their downward bent edges 46b and 47a and upward bent edges 44a and 46a may be alternately positioned, the dust and moisture from above will be prevented from entering into the apparatus and the safety will be maintained. Further, as the slider 33 and rail base 32 are prevented by the fixing screw 49 from moving relatively in the case of transporting the present apparatus, the lead screw 35 and gear will be prevented from being broken by various shocks caused during the transportation.

Figure 5:
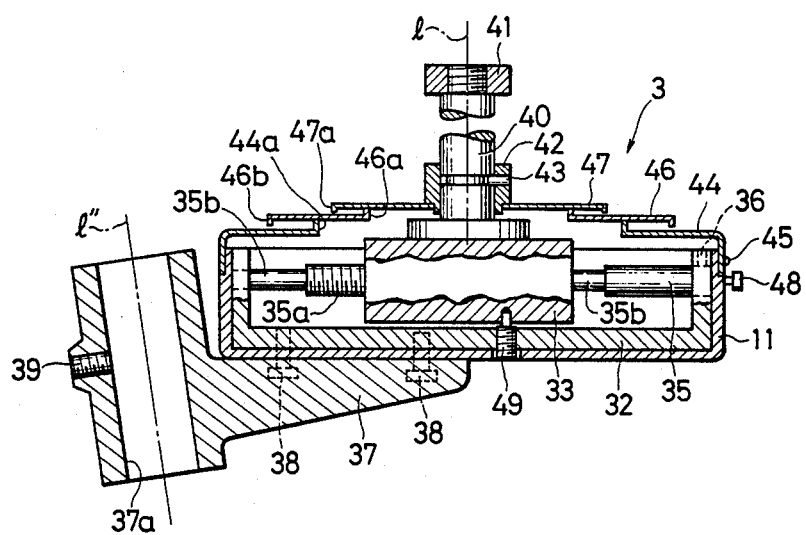
FIG. 5 is the same sectional view as FIG. 3, showing another embodiment of the present invention.

FIG. 5 shows another embodiment according to which the microscope assembly can be moved only in the Y-direction. The explanation of the formation and operation of this embodiment is omitted since those are substantially the same as described above.

I claim:

1. An operating microscope apparatus comprising a stand, a supporting arm mounted slidable and rotatably on said stand, a fitting shaft supported rotatably on said supporting arm, and a microscope assembly moving device fixed to said fitting shaft and mounting a microscope assembly, said microscope assembly moving device comprising a case supporting thereon said microscope assembly, a first member fixed to said fitting shaft, a second member slidably at touched to said case and mounted movably on said first member, a third member fixed to said second member, and a fourth member secured to said case and movable to said third member and movable in the direction perpendicular to the moving direction of said second member.

2. An operating microscope apparatus according to claim 1, in which said first and third members are sliders respectively and said second and fourth members are rail bases for guiding said first and third members respectively.

3. An operating microscope apparatus according to claim 1 or 2, in which said first and third members contain therein driving motors and gears connected to said driving motors respectively, and said second and forth members contain therein screws to said gears respectively.

4. An operating microscope apparatus according to claim 3 further comprising position detecting photocouplers on either one of said first and second members and of said third and fourth members and blade members giving position signals to said photocouplers in cooperation with said photocouplers respectively on the others of them.

5. An operating microscope apparatus according to claim 1 further comprising a plurality of covers movable integrally with said case and overlapped in steps to cover the upper portion of said case.

6. An operating microscope apparatus according to claim 5 in which said plurality of covers have respective bent edges engageable with one another.

7. An operating microscope apparatus according to claim 1 in which said operating microscope apparatus further comprises a suspending member secured to said case and supporting thereon said microscope assembly so that the incident optical axis of said microscope assembly coincides with the normal passing through the rotation center of said case when said case is in the center position of its moving range.

* * * * *